US011027097B2

(12) United States Patent
Haldis et al.

(10) Patent No.: US 11,027,097 B2
(45) Date of Patent: Jun. 8, 2021

(54) MONORAIL MIRCOCATHETER AND METHODS FOR USE

(71) Applicant: Sanford Health, Sioux Falls, SD (US)

(72) Inventors: Thomas Haldis, Horace, ND (US); Alexander Drofa, West Fargo, ND (US)

(73) Assignee: Sanford Health, Sioux Falls, SD (US)

( * ) Notice: Subject to any disclaimer, the term of this patent is extended or adjusted under 35 U.S.C. 154(b) by 167 days.

(21) Appl. No.: 15/870,943

(22) Filed: Jan. 13, 2018

(65) Prior Publication Data
US 2018/0200484 A1 Jul. 19, 2018

Related U.S. Application Data

(60) Provisional application No. 62/445,801, filed on Jan. 13, 2017.

(51) Int. Cl.
*A61M 25/01* (2006.01)
*A61M 25/10* (2013.01)
(Continued)

(52) U.S. Cl.
CPC ...... *A61M 25/0169* (2013.01); *A61M 25/104* (2013.01); *A61M 25/09041* (2013.01);
(Continued)

(58) Field of Classification Search
CPC .. A61M 2025/0004; A61M 2025/0037; A61M 2025/0063; A61M 2025/0183;
(Continued)

(56) References Cited

U.S. PATENT DOCUMENTS

| 5,203,338 | A | * | 4/1993 | Jang | A61B 8/12 600/434 |
| 6,022,319 | A | * | 2/2000 | Willard | A61M 25/0026 600/470 |
| 6,290,668 | B1 | * | 9/2001 | Gregory | A61B 18/245 604/22 |
| 2002/0082525 | A1 | * | 6/2002 | Oslund | A61M 25/0169 600/585 |

(Continued)

FOREIGN PATENT DOCUMENTS

| EP | 1201260 A1 | 5/2002 |
| WO | 2008008428 A1 | 1/2008 |

OTHER PUBLICATIONS

International Search Report for corresponding PCT Application No. PCT/US2018/013686, dated May 2, 2018.

*Primary Examiner* — Kathleen S Holwerda
*Assistant Examiner* — Brooke Labranche
(74) *Attorney, Agent, or Firm* — McDonnell Boehnen Hulbert & Berghoff LLP

(57) ABSTRACT

The present disclosure provides a catheter including a first tubular structure defining a first lumen, the first tubular structure having a first end and a second end. The catheter may also include a second tubular structure defining a second lumen, the second tubular structure having a first end and a second end. The catheter may also include an aperture between the first tubular structure and the second tubular structure. The aperture is located at the first end of the second tubular structure. A first portion of the first tubular structure extends beyond the aperture, and the second tubular structure is positioned adjacent to a second portion of the first tubular structure.

33 Claims, 8 Drawing Sheets

(51) Int. Cl.
    *A61M 25/00*        (2006.01)
    *A61M 25/09*        (2006.01)

(52) U.S. Cl.
    CPC ............ *A61M 2025/0004* (2013.01); *A61M 2025/0037* (2013.01); *A61M 2025/0063* (2013.01); *A61M 2025/0183* (2013.01); *A61M 2025/09125* (2013.01); *A61M 2025/1093* (2013.01)

(58) Field of Classification Search
    CPC .......... A61M 2025/09125; A61M 2025/1093; A61M 25/0169; A61M 25/09041; A61M 25/104
    See application file for complete search history.

(56) References Cited

U.S. PATENT DOCUMENTS

| | | | | |
|---|---|---|---|---|
| 2003/0040769 | A1* | 2/2003 | Kelley | A61M 25/0075 606/194 |
| 2003/0153934 | A1* | 8/2003 | Gerberding | A61M 25/0169 606/157 |
| 2003/0191434 | A1* | 10/2003 | Dorros | A61B 17/22 604/101.04 |
| 2004/0153049 | A1 | 8/2004 | Hewitt | |
| 2004/0186505 | A1 | 9/2004 | Joergensen | |
| 2012/0046646 | A1 | 2/2012 | Schwager | |
| 2012/0265283 | A1* | 10/2012 | Mack | A61M 25/1011 623/1.11 |
| 2013/0281787 | A1* | 10/2013 | Avneri | A61M 25/0133 600/208 |
| 2017/0182290 | A1* | 6/2017 | Stern | A61M 25/005 |

\* cited by examiner

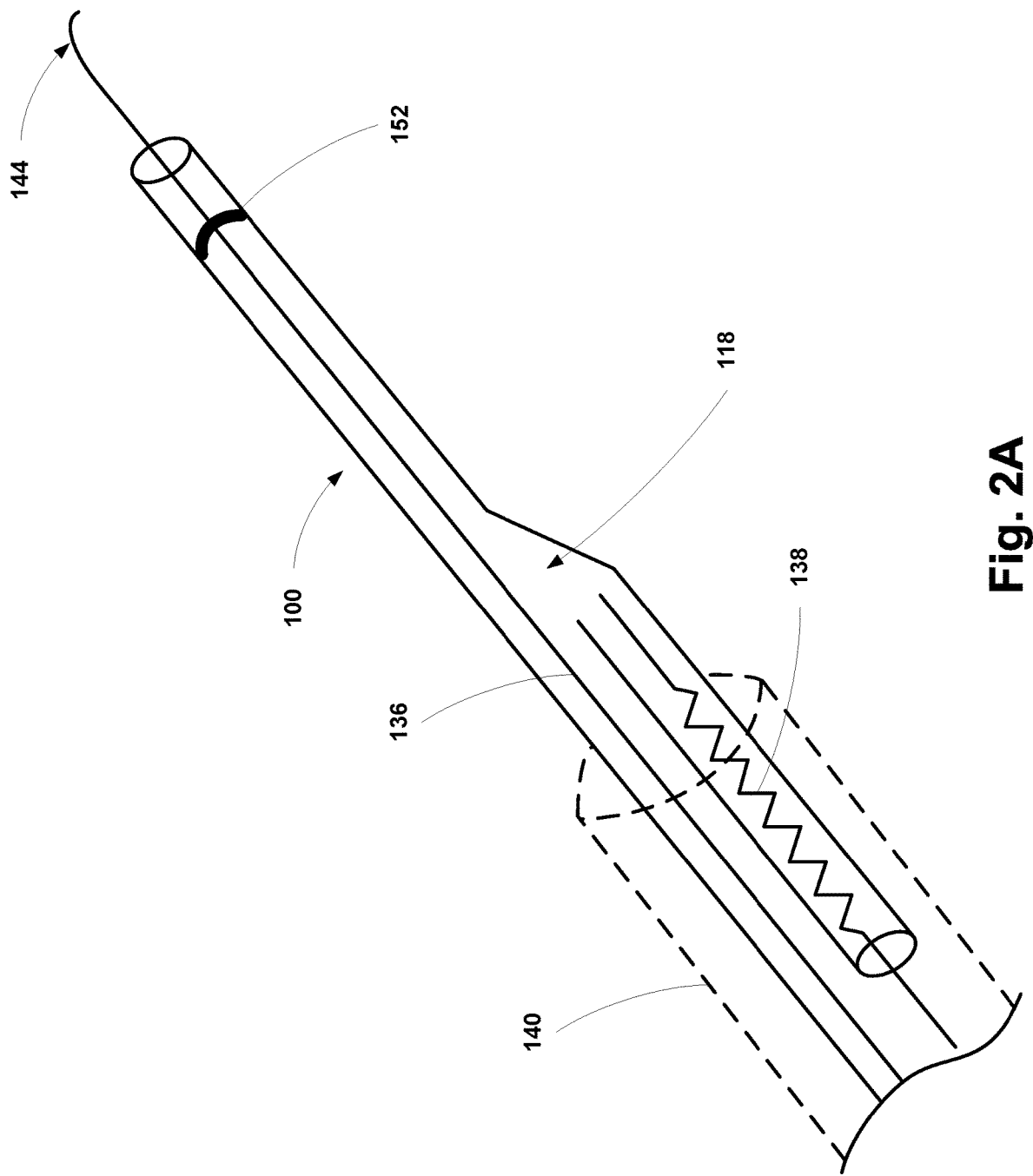

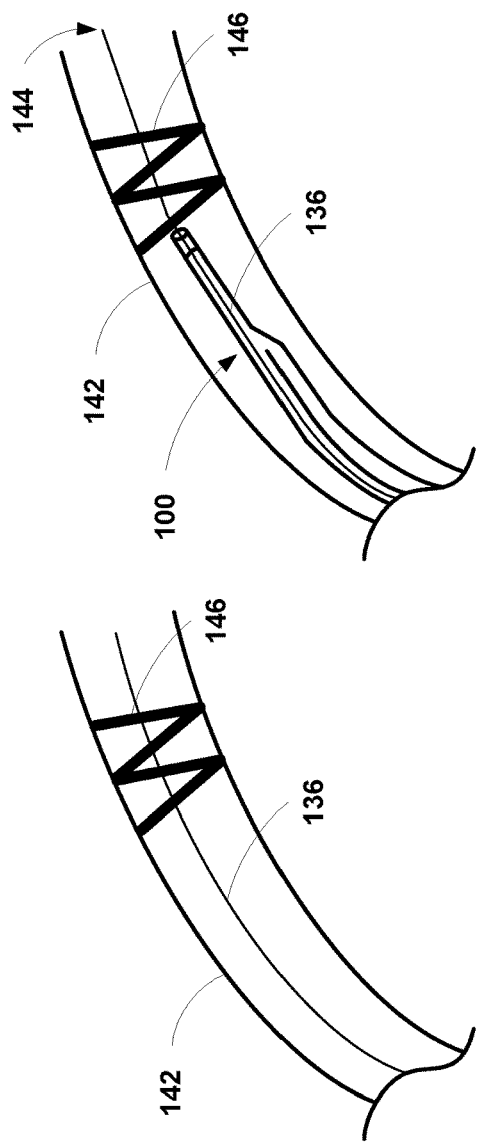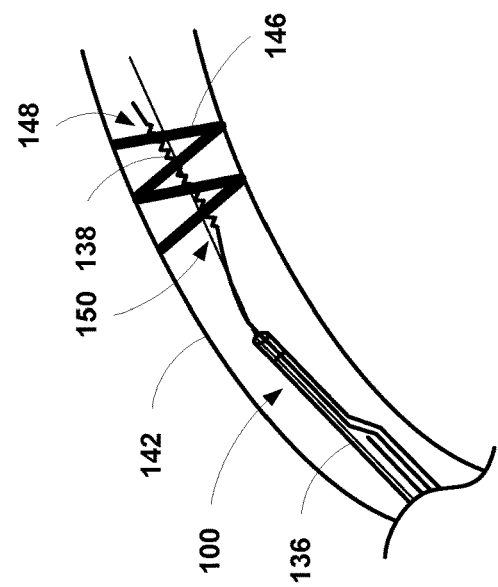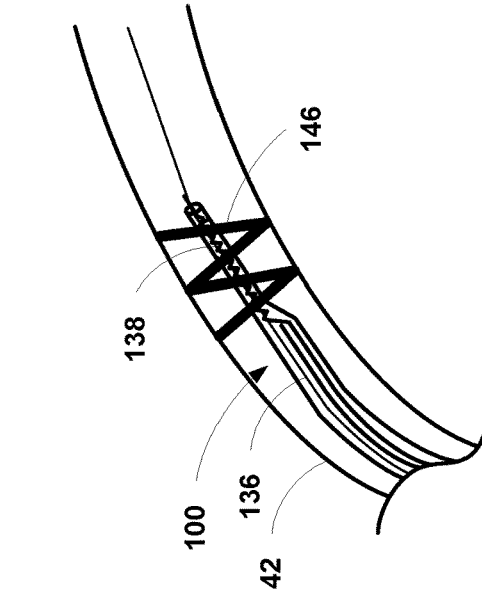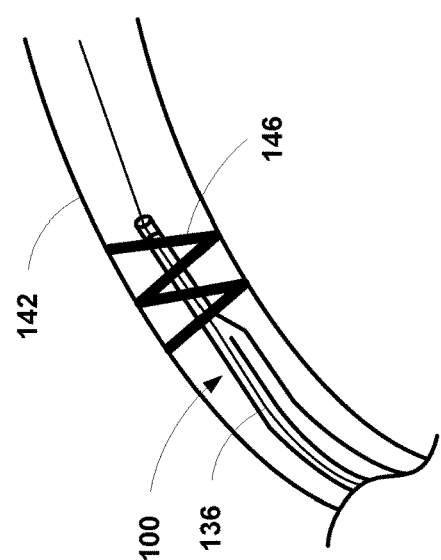

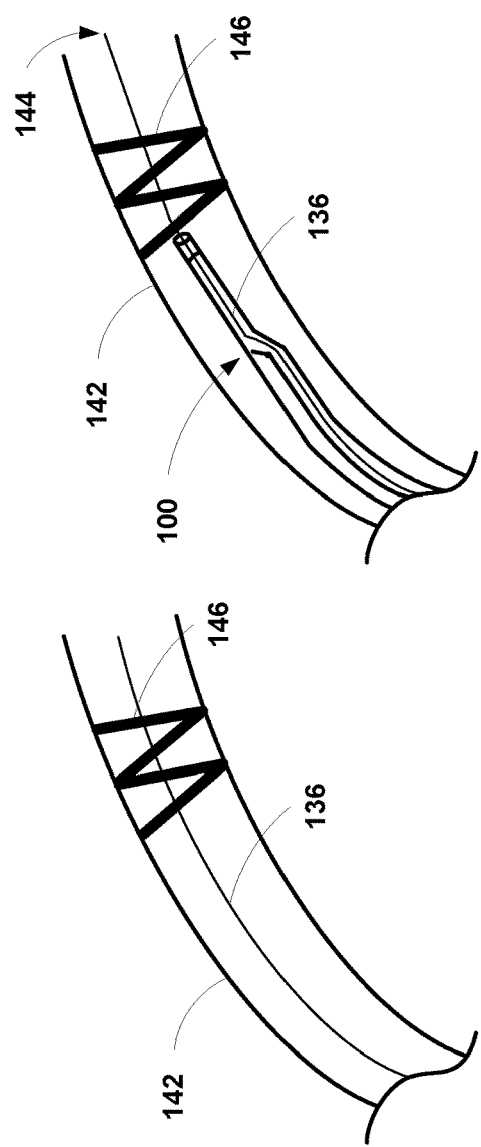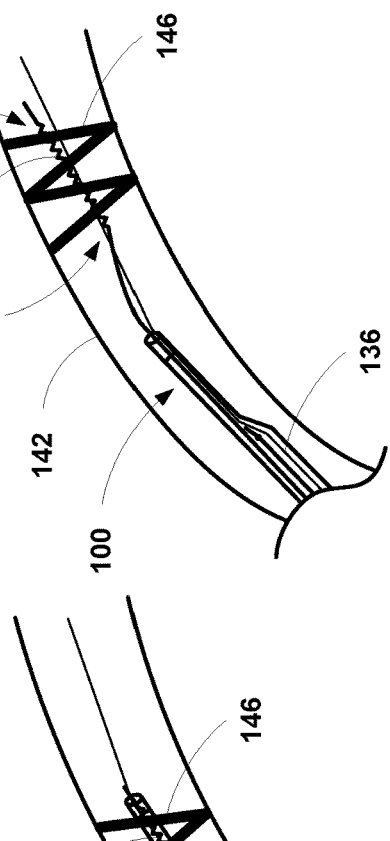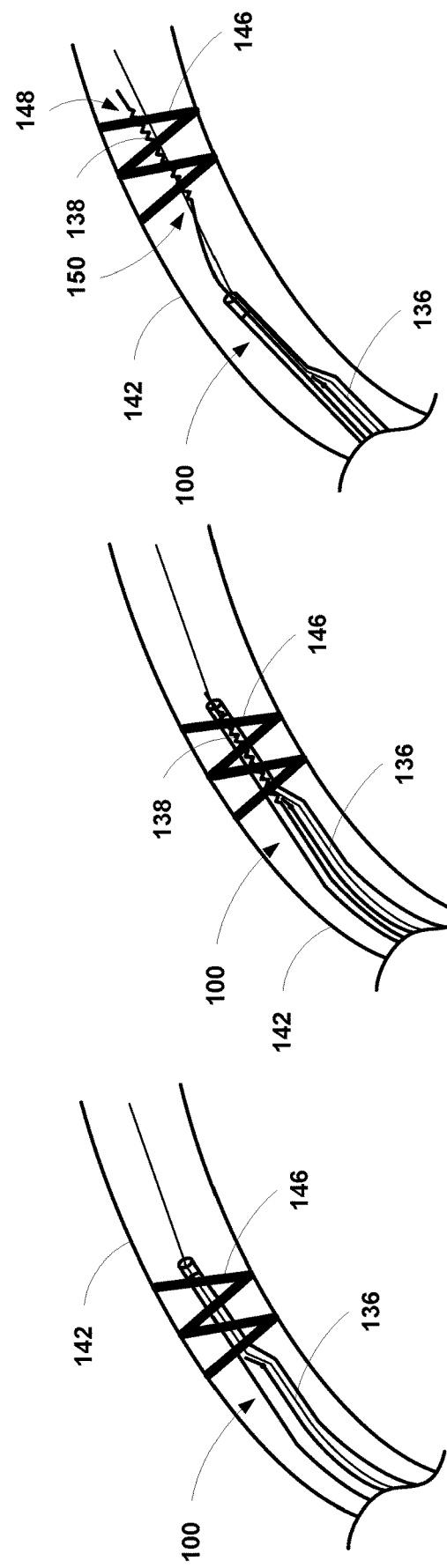

MONORAIL MIRCOCATHETER AND METHODS FOR USE

RELATED APPLICATIONS

This application claims the benefit of priority to U.S. Provisional Application No. 62/445,801 entitled "Dual-Lumen Microcatheter and Methods for Use," filed on Jan. 13, 2017, the contents of which are hereby incorporated by reference in their entirety.

BACKGROUND THE INVENTION

Cerebral blood flow is critical in human anatomy. If blood flow is blocked to the brain, the tissue that does not receive blood flow will become ischemic and begin to die. The result is either a deficit in cognition, function, or even death. The results are also irreversible if such an ischemia lasts too long. The period of time can vary from patient to patient, but typically if blood flow to the brain is not restored after approximately 4.5 hours, an ischemic stroke may occur. These ischemic strokes can happen in any of the cerebral arteries, but are most common in the middle cerebral artery. Traditionally, such middle cerebral artery acute ischemic strokes have been devastating to the patient.

Around 1995, the use of tissue plasminogen activator (tPA), a lytic agent, was introduced as the first treatment for ischemic stroke. The tPA brakes down unorganized acute clot. This procedure provided moderate reduction in morbidity and mortality and has been the main stay in acute ischemic stroke treatment until just recently. In 2015, a new approach was approved in the United States known as mechanical thrombectomy. In this approach, a revascularization device, such as a stent retriever, is deployed within an occlusion, the stent struts spread into the occlusion, then the occlusion is drawn back into the catheter under suction and removed from the body. This mechanical thrombectomy approach has reduced the mortality rate to around 20% for patients who are treated within the critical time window.

While outcomes are significantly improved, the mechanical thrombectomy procedure is still labor intensive. The mechanical thrombectomy device is either introduced through a femoral or carotid access. If the device is introduced from a femoral access, the operator needs to navigate the aortic anatomy with a special focus on the aortic arch. Aortic arches can be difficult to navigate, especially with type three aortic arches. Once the occlusion is reached and crossed, the occlusion can be treated. However, reaching the occlusion can be a significant challenge due to the tortuous nature of various arteries, such as the cerebral and coronary arteries as examples. Such a procedure may require multiple catheter and wire changes in order to advance the revascularization device.

The commonly held belief is that in order to restore flow across the blockage, approximately 1.7 passes of the revascularization device per vessel are required. In order to advance the revascularization device to the occlusion for the first device deployment, the guidewire must be removed from the patient. As a result, if a second device deployment is needed, the operator must again advance the guidewire and microcatheter back through the tortuous cerebral arteries, which may be very challenging and time consuming. Further, in addition to use in revascularization in a mechanical thrombectomy as described above, the device as described herein could be used for pulmonary embolism, peripheral arterial thrombectomy, and deep venous thrombosis clot retrieval. Therefore, an improved catheter for delivery of a revascularization device may be desirable.

SUMMARY OF THE INVENTION

Thus, in a first aspect, the present invention provides a catheter comprising: (a) a first tubular structure defining a first lumen, the first tubular structure having a first end and a second end, (b) a second tubular structure defining a second lumen, the second tubular structure having a first end and a second end, and (c) an aperture between the first tubular structure and the second tubular structure, the aperture located at the first end of the second tubular structure, where a first portion of the first tubular structure extends between the aperture and the first end of the first tubular structure, and where a second portion of the first tubular structure is coupled to and along a length of the second tubular structure.

In a second aspect, the present invention provides a catheter comprising: (a) a tubular structure defining a lumen, the tubular structure having a first end and a second end, where the first end of the tubular structure comprises a first opening, and where the second end of the tubular structure comprises a second opening, and (b) a wire tip extending from the first end of the tubular structure, where the wire tip includes a first portion coupled to the first end of the tubular structure and a second portion extending away from the first portion, where a stiffness of the second portion of the wire tip is less than a stiffness of the first portion of the wire tip.

In a third aspect, the present invention provides a method comprising: (a) introducing a catheter according to the first aspect and a guidewire together into an arterial configuration, where a distal end of the guidewire extends distal to the first end of the first tubular structure, (b) advancing the catheter and the guidewire together through the arterial configuration until the distal end of the guidewire is advanced across an occlusion in the arterial configuration, (c) advancing the catheter with respect to the guidewire in the arterial configuration such that the first end of the first tubular structure is advanced across the occlusion, (d) retracting the distal end of the guidewire into the first tubular structure through the aperture and into the second tubular structure, (e) advancing a revascularization device through the second end of the first tubular structure to the first end of the first tubular structure, and (f) retracting the catheter relative to the neovascularization device such that the revascularization device is deployed into the arterial configuration with a first end of the revascularization device located distal to the occlusion and a second end of the revascularization device located proximal to the occlusion.

In a fourth aspect, the present invention provides a method comprising: (a) introducing a guidewire into an arterial configuration and through an occlusion via arterial access, (b) loading the catheter according to the first aspect onto the guidewire, such that a proximal end of the guidewire enters the catheter at the first end of the first tubular structure, advances past the aperture and into the second portion of the first tubular structure and exits at the second end of the first tubular structure, (c) advancing the catheter along the guidewire and introducing the catheter into the arterial configuration such that the first end of the first tubular structure is advanced across the occlusion, (d) advancing a revascularization device through the second end of the second tubular structure, through the aperture, and into the first end of the first tubular structure, and (e) retracting the catheter relative to the neovascularization device such that the revascularization device is deployed into the arterial configuration with a first end of the revascularization device located distal to the occlusion and a second end of the revascularization device located proximal to the occlusion In a fifth aspect, the present invention provides a method comprising: (a) introducing a guidewire into an arterial configuration and through an occlusion via arterial access, (b) loading the catheter according to the first aspect onto the guidewire, such that a proximal end of the guidewire enters the catheter at the first end of the first tubular structure, advances through the aperture and into the second lumen of the second tubular structure and exits at the second end of the second tubular structure, (c) advancing the catheter along the guidewire and introducing the catheter into the arterial configuration such that the first end of the first tubular structure is advanced across the occlusion, (d) advancing a revascularization device through the second end of the first tubular structure to the first end of the first tubular structure, and (e) retracting the catheter relative to the neovascularization device such that the revascularization device is deployed into the arterial configuration with a first end of the revascularization device located distal to the occlusion and a second end of the revascularization device located proximal to the occlusion.

In a sixth aspect, the present invention provides a method comprising: (a) introducing a catheter according the second aspect into an arterial configuration such that the wire tip is advanced across an occlusion, where a first end of the first portion of the wire tip is located distal to the occlusion and a second end of the first portion of the wire tip is located proximal to the occlusion when the wire tip is advanced across the occlusion, (b) advancing a revascularization device through the second end of the tubular structure to the first end of the first tubular structure, and (c) advancing the revascularization device across the occlusion such that the revascularization device is deployed into the arterial configuration with a first end of the revascularization device located distal to the occlusion and a second end of the revascularization device located proximal to the occlusion.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 2A illustrates an example dual-lumen catheter with a guidewire positioned in the first lumen and a revascularization device positioned in the second lumen, according to an example embodiment.

FIGS. 5A-5E illustrate alternative method steps of using the dual-lumen catheter of FIG. 2A, according to an example embodiment.

FIGS. 6A-6E illustrate alternative method steps of using the dual-lumen catheter of FIG. 2B, according to an example embodiment.

DETAILED DESCRIPTION OF THE INVENTION

Figure 1:
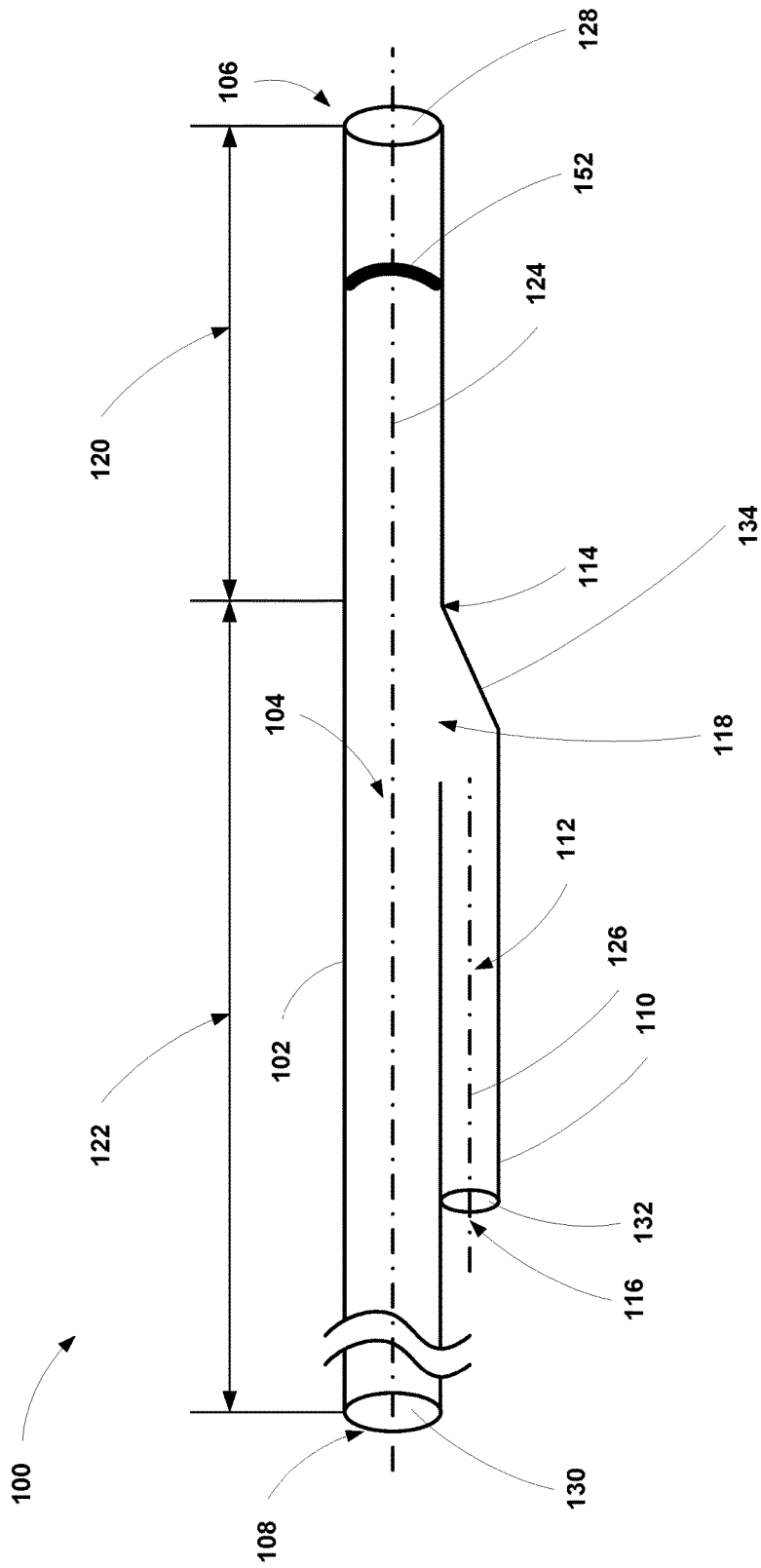
FIG. 1 illustrates a dual-lumen catheter, according to an example embodiment.

Exemplary devices and methods are described herein. It should be understood that the word "exemplary" is used herein to mean "serving as an example, instance, or illustration." Any embodiment or feature described herein as "exemplary" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

As used herein, with respect to measurements, "about" means +/−5%.

As used herein, a "catheter" is an apparatus that is connected to a deployment mechanism and is configured to house a medical device that can be delivered over a guidewire. The catheter may include a guidewire lumen for over-the-wire guidance and may be used for delivering the medical device to a target lumen. A catheter can have braided metal strands within the catheter wall for increased structural integrity. The structural elements of the catheter tip can be bonded or laser welded to the braided strands of the catheter to improve the performance characteristics of the catheter tip.

As used herein, a "guidewire" is an elongated cable comprised of one or more biocompatible materials including metals and polymers. Guidewires may be used for selecting target lumens and guiding catheters to target deployment locations. Guidewires are typically defined as wires used independently of other devices that do not come as part of an assembly.

As used herein, a "revascularization device" is a device, like a stent retriever, that is advanced through emboli in the form of an occlusion and configured to expand and embed in the emboli. Once embedded in the occlusion, the revascularization device may then be retracted to restore blood flow and aid thrombectomy in acute embolic stroke.

As used herein, "lumen" refers to a passage within an arterial or tubular structure, such as the cerebral or coronary arteries or a passage within the tubular structures or catheters through which the guidewire may be disposed.

As used herein, "deployment" refers to when a catheter has been positioned in the target lumen and is actively being used.

As used herein, "first end" refers to a distal end of the device or component thereof, and "second end" refers to a proximal end of the device or component thereof.

As used herein, "distal" with respect to a portion of the apparatus means the end of the device (when in use) nearer the treatment zone (e.g., the cerebral or coronary arteries) of the subject and the term "proximal" means the portion of the device (when in use) further away from the targeted lumen of the subject and nearer the access site and the operator.

As used herein, "arterial configuration" refers to any segment of the arterial tree.

As used herein, a "longitudinal axis" of a lumen is a long axis running the length of the lumen through its center.

As used herein, "biocompatible material" means any suitable biocompatible material, either synthetic or biologic, such as titanium, nitinol, polypropylene, polyethylene terephthalate (PET), Poly-4-hydroxybutyrate (P4HB) and Polytetrafluoroethylene (PTFE).

As used herein, "coupled" means associated directly as well as indirectly. For example, a member A may be directly associated with a member B, or may be indirectly associated therewith, e.g., via another member C. It will be understood that not all relationships among the various disclosed elements are necessarily represented.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

With respect to the Figures, an example catheter 100 may include a first tubular structure 102 defining a first lumen 104, the first tubular structure 102 having a first end 106 and a second end 108, as shown in FIG. 1. The catheter 100 may also include a second tubular structure 110 defining a second lumen 112, the second tubular 110 structure having a first end 114 and a second end 116. The catheter also includes an aperture 118 between the first tubular structure 102 and the second tubular structure 110, the aperture 118 located at the first end 114 of the second tubular structure 110. As shown in FIG. 1, a first portion 120 of the first tubular structure 102 extends between the aperture 118 and the first end 114 of the first tubular structure 102, and a second portion 122 of the first tubular structure 102 is coupled to and along a length of the second tubular structure 110. In particular, as shown in FIG. 1, the first portion 120 of the first tubular structure 102 begins just distal to the most distal portion of the aperture 118 and extends in a distal direction to the first end 106 of the first tubular structure 102.

The design of the catheter 100 as described above allows for the second tubular structure 110 in the catheter 100 to be used to maintain wire access across an occlusion 146 while performing a revascularization procedure. The benefit is that the guidewire 136 is "out of the way" of the revascularization device 138, and the guidewire 136 does not have to be completely removed and then re-advanced after the procedure is complete. This advancement eliminates the need to repeatedly cross the occlusion 146 with the guidewire 136 and reduces associated complications. With this approach, the operator effectively never loses wire access or microcatheter access across the occlusion 146, saving significant time and potentially improving safety of the procedure for the patient. This technology also eliminates the need to reload a second revascularization device from the first tubular structure 102 of the catheter 100, which may be timely and cumbersome.

As shown in FIG. 1, a longitudinal axis 124 of the first lumen 104 is parallel to a longitudinal axis 126 of the second lumen 112 at a given location along the length of the first tubular structure 102 and the second tubular structure 110. In particular, the longitudinal axis 124 of the first lumen 104 is parallel to the longitudinal axis 126 of the second lumen 112 until the two lumens 104, 112 connect via the aperture 118. In addition, the first end 106 of the first tubular structure 102 includes a first opening 128, the second end 108 of the first tubular structure 102 includes a second opening 130, and the second end 116 of the second tubular structure 110 includes a third opening 132.

The first lumen 104 may have a length ranging from about 30 cm to about 170 cm. A diameter of the second portion 122 of the first tubular structure 102 may have a range from about 0.35 mm to about 6 mm. The second tubular structure 110 may have a length ranging from about 5 cm to about 160 cm. The diameter of the second tubular structure 110 may have a range from about 0.25 mm to about 1.2 mm. The length of the second tubular structure 110 may be coextensive with the second portion 122 of the first tubular structure 102. In various alternative embodiments, the length of the second tubular structure 110 may be shorter than the second portion 122 of the first tubular structure 102 thereby reducing the catheter's footprint. Such an embodiment is shown in FIG. 1. In such an embodiment, even if a guidewire 136 were to inadvertently retract out of the second end 116 of the second lumen 112 of the second tubular structure 110, the ability to re-select the second lumen 112 without having to fully retract and then fully redeploy the guidewire would still provide time savings. In such an example, the guidewire simply resides in the arterial configuration. Similar to coronary monorail balloon and stent catheters, the shorter second lumen 112 shown in FIG. 1 may allow for the use of a shorter wire and may help make catheter exchanges faster. In such an embodiment, the shorter second tubular structure 110 may have a third opening 132 at the proximal second end 116 that remains positioned in the body, and the longer first tubular structure 102 may have a proximal second opening 130 that is externalized with respect to the body. The first portion 120 of the first tubular structure 102 may have a length ranging from about 3 cm to about 25 cm. The diameter of the first portion 120 of the first tubular structure 102 may have a range from about 0.35 mm to about 6 mm.

A portion of the catheter 100 at the first end 106 may include one or more curved sections, such as a first bend and a second bend as an example. The first bend and the second bend may accommodate known curves of the target arterial configuration, such as the coronary artery or cerebral artery, as examples. In one particular example, the first portion 120 of the first tubular structure 102 may be pre-curved. The radius of curvature may vary in order to navigate the variable patient anatomy. In particular, the first portion 120 of the first tubular structure 102 has a radius of curvature ranging from about 0 mm to about 170 mm.

In another embodiment, the catheter 100 includes a locking device 152 configured to prevent the catheter 100 from moving with respect to the guidewire 136 in a locked mode, and the locking device 152 is configured to allow the catheter 100 to move along the guidewire 136 in an unlocked mode. In one example, such a locking device 152 may comprise a torque lock positioned at the first end 106 of the first tubular structure 102. Such a torque lock may comprise a small cylindrical apparatus that is made of polymers and that can be advanced over the guidewire 136 until adjacent to the catheter handle. When torqued, the torque lock may squeeze the guidewire 136 effectively preventing the catheter 100 from sliding over the distal end 144 of the guidewire 136. In another embodiment, the locking device 152 may comprise a tuohy-borst adapter that can be tightened over an externalized part of the guidewire 136. In use, the guidewire 136 may pass through a center of the tuohy-borst adapter, and a rotatable component may be rotated to thereby tighten the tuohy-borst adapter around the wire to prevent the catheter 100 from sliding over the distal end 144 of the guidewire 136. Other locking devices are possible as well.

In one embodiment, a stiffness of the first portion 120 of the first tubular structure 102 is less than a stiffness of the second portion 122 of the first tubular structure 102 and the stiffness of the second tubular structure 110. In such an example, the second portion 122 of the first tubular structure 102 and the second tubular structure 110 include a first material, and the first portion 120 of the first tubular structure 102 includes a second material that is different than the first material. For example, the first material may include a plurality of metal strands that make the second portion 122 of the first tubular structure 102 and the second tubular structure 110 more stiff than the first portion 120 of the first tubular structure 102. In one example, the metal strands are braided. Braided metal strands may provide increased structural integrity. In another example, the metal strands may include strips. In one embodiment, a portion of the plurality of metal strands arranged along the second portion 122 of the first tubular structure 102 and the second tubular structure 110 are wider than a portion of the plurality of metal strands arranged along the first portion 120 of the first tubular structure 102. In another embodiment, a portion of the plurality of metal strands arranged along the second portion 122 of the first tubular structure 102 and the second tubular structure 110 are thicker than a portion of the plurality of metal strands arranged along the first portion 120 of the first tubular structure 102.

In one particular example, the second portion 122 of the first tubular structure 102 and the second tubular structure 110 comprise an elastomer outer layer, a metal middle layer (e.g., a metal layer), and an inner hydrophilic polymer layer (e.g., PTFE). The metal layer stiffens the second portion 122 of the first tubular structure 102 and the second tubular structure 110 to provide support for passage of a medical device, while at the same time increasing the stiffness of the second portion 122 of the first tubular structure 102 and the second tubular structure 110. The result is that the first portion 120 of the first tubular structure 102 is more easily adapted to tortuous anatomy. The metal layer may comprise a plurality of metal strands arranged longitudinally or helically along at least a portion of the length of one or more of the first tubular structure 102 and the second tubular structure 110. The plurality of metal strands may comprise stainless steel, cobalt chromium, nitinol, or a combination thereof. The elastomer outer layer may provide flexibility and support to the second portion 122 of the first tubular structure 102 and the second tubular structure 110, while the middle layer provides strength, increasing kink-resistance, and improving torqueing of the second portion 122 of the first tubular structure 102 and the second tubular structure 110. The inner layer may include a lubricious coating that reduces friction between the catheter 100 and a revascularization device and a guidewire.

The first portion 120 of the first tubular structure 102 may not include the metal layer, or the metal layer may be looser than the metal layer of the second portion 122 of the first tubular structure 102 and the second tubular structure 110, thereby causing the stiffness of the first portion 120 of the first tubular structure 102 to be less than the stiffness of the second portion 122 first tubular structure 102 and the second tubular structure 110. In another example, the first portion 120 of the first tubular structure 102 includes an elastic material that is configured to hug the guidewire as the catheter 100 negotiates arterial bends and to avoid the catheter 100 hanging up on side branches.

In another example, a thickness of the first portion 120 of the first tubular structure 102 may be less than a thickness of the second portion 122 of the first tubular structure 102 and a thickness of the second tubular structure 110. In such an example, the first portion 120 of the first tubular structure 102, the second portion 122 of the first tubular structure 102, and the second tubular structure 110 may each comprise the same material(s), and the varying thicknesses provide the difference in stiffness. In another example, as described above, the thickness of the first portion 102 of the first tubular structure 102, the thickness of the second portion 122 of the first tubular structure 102, and the thickness of the second tubular structure 110 may be the same, while the difference in material(s) provides the difference in stiffness between the components. In another example, the first portion 120 of the first tubular structure 102 may have differential stiffness throughout; the second (proximal) end may be the stiffest and gradually softens towards the first end (distal tip) 106.

As shown in FIG. 1, the catheter 100 may further comprise an angled surface 134 positioned at the first end 114 of the second tubular structure 110, thereby providing an angled transition from the second lumen 112 to the first lumen 104 through the aperture 108. In operation, the angled surface 134 may assist in guiding a guidewire through the aperture 118 located at the first end 114 of the second tubular structure 110 and into the lumen 104 of the first tubular structure 102. The angled surface 134 may have an angle ranging from about 10 degrees relative to the longitudinal axis 126 of the second lumen 112 to about 80 degrees relative to the longitudinal axis 126 of the second lumen 112. In another example, the catheter 110 may further comprise a rounded surface, instead of the angled surface 134, positioned at the first end 114 of the second tubular structure 110, thereby providing a rounded transition from the second lumen 112 to the first lumen 104 through the aperture 118.

In one embodiment, the first portion 120 of the first tubular structure 102 is tapered. Such an embodiment may be advantageous in that the first portion 120 of the first tubular structure 102 may be configured to sufficiently hug the guidewire. The vessels taper as the catheter 100 travels more distal in the vascular tree. Therefore, a taper on the first portion 120 of the first tubular structure 102 may help negotiate bends and avoid snagging on side branches. In another embodiment, the first portion 120 of the first tubular structure 102 includes a variable diameter. Such a configuration may help accommodate the guidewire 136 and the revascularization device 138 without increasing the size of the catheter 100 and decreasing maneuverability and flexibility which may occur with a larger sized catheter. In one example, the variable diameter of the first portion 120 of the first tubular structure 120 may be accomplished by including an expandable elastomer in that section of the catheter 100. In another example, the variable diameter of the first portion 120 of the first tubular structure 102 may be accomplished by including a c-shape for that portion of the catheter 100 having a gap that permits the c-shape to close and widen the gap in response to external force from the walls of the vessels in which the catheter is being advanced. In yet another example, the variable diameter of the first portion 120 of the first tubular structure 102 may be accomplished by both including an expandable elastomer having a c-shape in that portion of the catheter 100. Other examples are possible as well.

FIG. 2A illustrates an example dual-lumen catheter 100 with a guidewire 136 positioned in the first lumen 104 of the first tubular structure 102 and a revascularization device 138 positioned in the second lumen 112 of the second tubular structure 110. As shown in FIG. 2A, the catheter 100 may be positioned within an intermediate catheter 140 for delivery to the desired arterial configuration. Such an arrangement may be used in the methods shown and described in FIGS. 5A-5E below.

Figure 2B:
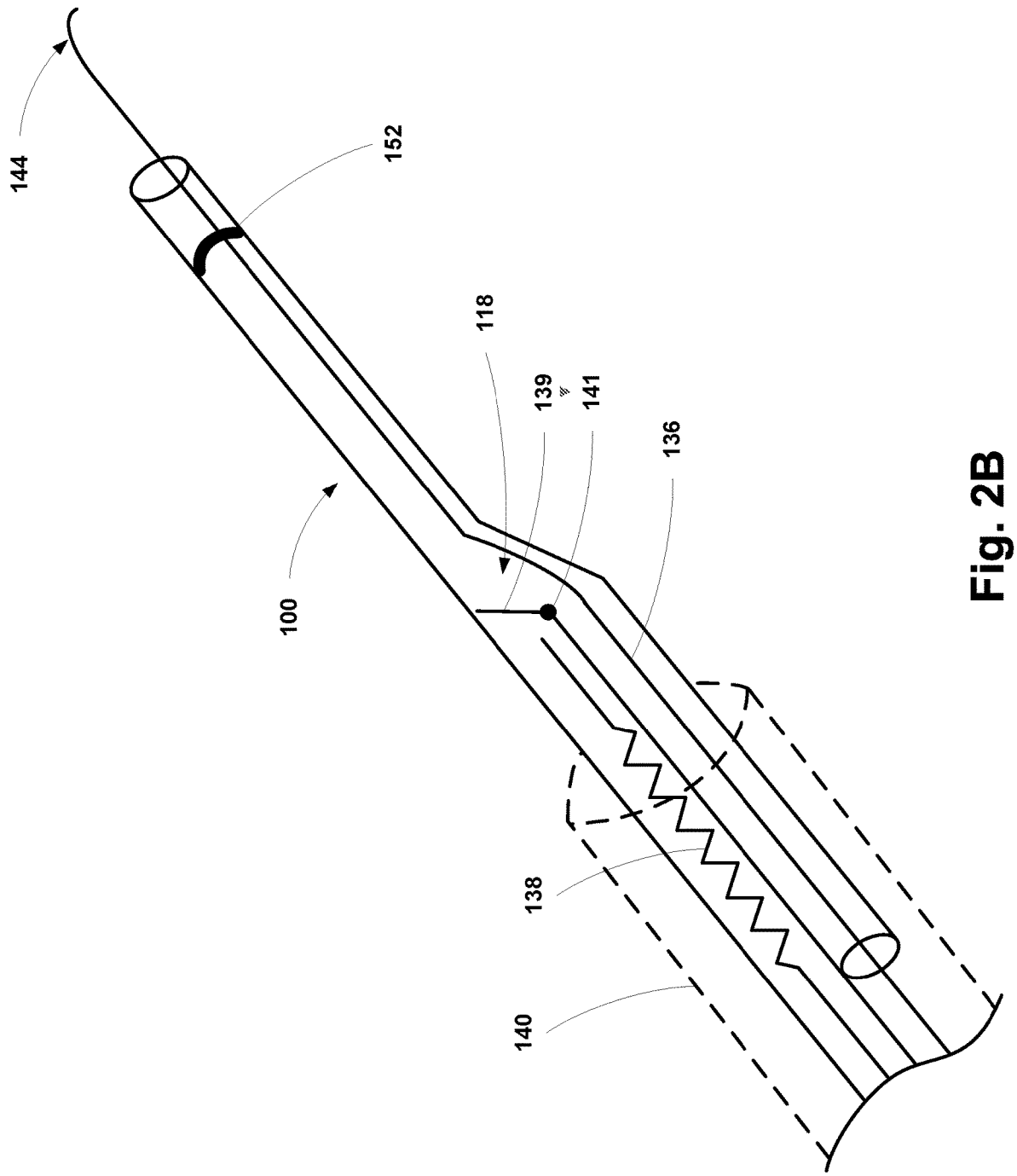
FIG. 2B illustrates an example dual-lumen catheter with a revascularization device positioned in the first lumen and a guidewire positioned in the second lumen, according to an example embodiment.

FIG. 2B illustrates an example dual-lumen catheter 100 with a revascularization device 138 positioned in the first lumen 104 of the first tubular structure 102 and a guidewire 136 positioned in the second lumen 112 of the second tubular structure 110. As shown in FIG. 2B, the catheter 100 may be positioned within an intermediate catheter 140 for delivery to the desired arterial configuration. Further, the catheter 100 shown in FIG. 2B may further include a baffle 139. The baffle 139 may include a rigid structure coupled to an interior surface of the first tubular structure 102. As such, the baffle 139 may be configured to at least partially obstruct the first lumen 104 of the first tubular structure 102, such that when the catheter 100 is backloaded onto the guidewire 136, the guidewire 136 contacts the baffle 139 and is thereby directed through the aperture 118 and into the second lumen 112 of the second tubular structure 110. The baffle 139 may be rotatably coupled to the interior surface of the first tubular structure 102, such that when the revascularization device 138 is advanced through the first lumen 104 to the first end 106 of the first tubular structure 102, the baffle 139 rotates about a pivot 141 to allow the revascularization device 138 past the baffle 139. In one example, the baffle 139 comprises a cantilever beam that is fixed to the interior surface of the first tubular structure 102. In another example, the pivot 141 comprises a spring that biases the baffle to the position shown in FIG. 2B. Other examples are possible as well. The arrangement of FIG. 2B may be used in the methods shown and described in FIGS. 6A-6E below.

Figure 3:
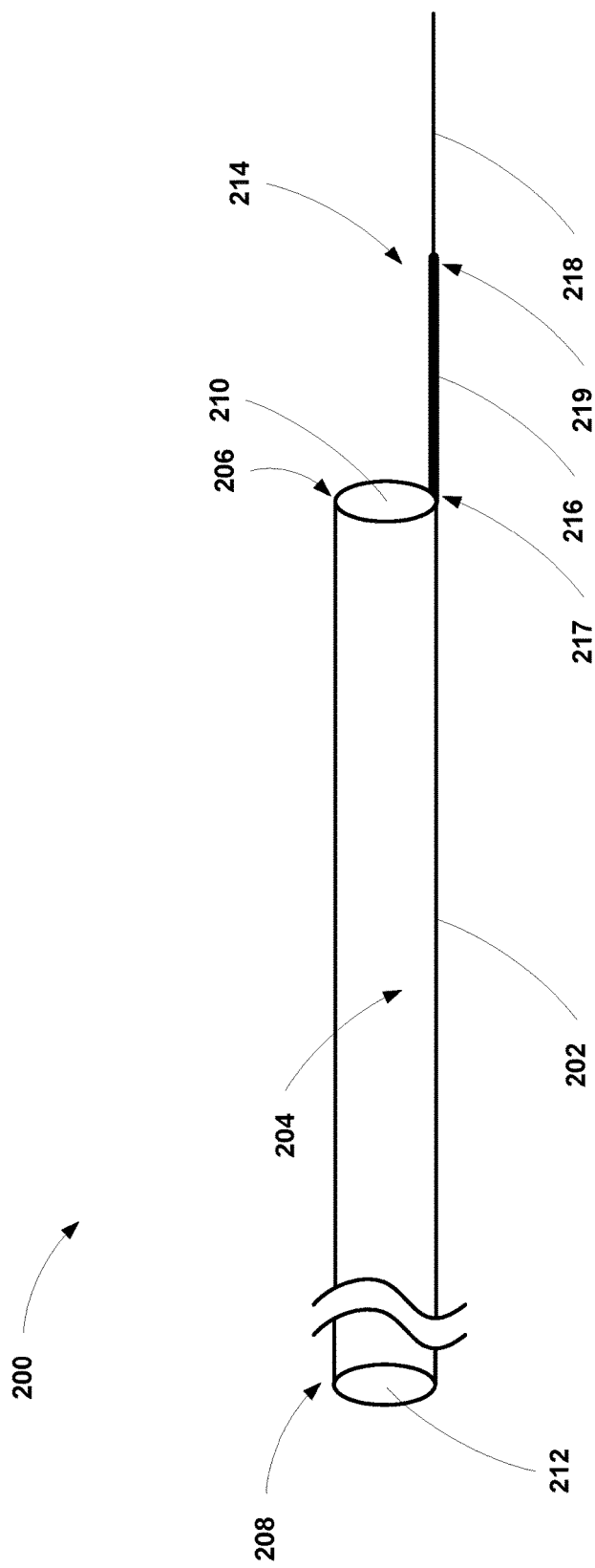
FIG. 3 illustrates another catheter, according to an example embodiment.

Another example catheter 200 is shown in FIG. 3. As shown in FIG. 3, the catheter 200 includes a tubular structure 202 defining a lumen 204 and having a first end 206 and a second end 208. The first end 206 of the tubular structure 202 comprises a first opening 210, and the second end 208 of the tubular structure 202 comprises a second opening 212. The catheter 200 also includes a wire tip 214 extending from the first end 206 of the tubular structure 202. As shown in FIG. 3, the wire tip 214 includes a first portion 216 coupled to the first end 206 of the tubular structure 202 and a second portion 218 extending away from the first portion 216. The first portion 216 of the wire tip 214 includes a first end 217 and a second end 219. The wire tip 214 may be fixed with respect to the tubular structure 202, such that both the tubular structure 202 and the wire tip 214 move together as a unitary structure. In operation, the wire tip 214 enables the operator to more easily guide the catheter 200 to the desired location.

A stiffness of the second portion 218 of the wire tip 214 is less than a stiffness of the first portion 216 of the wire tip 214. In one example, the first portion 216 of the wire tip 214 comprises a first material, and the second portion 218 of wire tip 214 comprises a second material that is different than the first material. The second material may be a more compliant material, and the first material may be a stiffer material. In another example, the first material may include a coating surrounding the second portion 218 of the wire tip 214. In another example, a thickness of the first portion 216 of the wire tip 214 is greater than a thickness of the second portion 218 of the wire tip 214. In such an example, the first portion 216 of the wire tip 214 and the second portion 218 of the wire tip 214 may each comprise the same material(s), and the varying thicknesses provide the difference in stiffness. In another example, as described above, the thickness of the first portion 216 of the wire tip 214 and the second portion 218 of the wire tip 214 may be the same, while the difference in material(s) provides the difference in stiffness between the components. In another example, the wire tip 214 may have differential stiffness throughout; the proximal end of the first portion 216 of the wire tip 214 may be the stiffest and gradually softens towards the distal end of the second portion 218 of the wire tip 214.

The lumen 204 of the tubular structure 202 may have a length ranging from about 30 cm to about 170 cm, and a diameter of the tubular structure 202 may have a range from about 0.35 mm to about 6 mm. A portion of the catheter 200 at the first end 206 may include one or more curved sections, such as a first bend and a second bend as an example. The first bend and the second bend may accommodate known curves of the target arterial configuration, such as the coronary artery or cerebral artery, as examples. In one particular example, a portion of the first end 206 of the tubular structure 202 may be pre-curved. The radius of curvature may vary in order to navigate the variable patient anatomy. In particular, the first end 206 of the tubular structure 202 may have a radius of curvature ranging from about 0 mm to about 170 mm.

In one embodiment, the wire tip 214 is substantially straight. Such an arrangement may make loading the catheter 200 into an intermediate catheter easier. The substantially straight wire tip 214 allows the operator loading the catheter 200 into an intermediate catheter to get the catheter 200 started in the intermediate catheter before trying to advance the catheter 200. The substantially straight wire tip 214 also makes advancing the catheter 200 through an intermediate catheter easier. If the terminal extent of the wire tip 214 were coiled, the coiled nature would push the tip into the inner surface of the intermediate catheter making advancement of the catheter 200 challenging. Instead, the substantially straight wire tip 214 enables the operator to more easily guide the catheter 200 to the desired location. In some examples, the wire tip 214 may extend beyond the first end 206 of the tubular structure 202 at a length of about 2 mm to about 200 mm, and preferably a length of about 3 mm to about 50 mm.

Additionally, the wire tip 214 may be shaped or constructed in such a way as to mitigate inadvertent injury to portions of the lumen with which the wire tip 214 comes into contact. For instance, the second portion 218 of the wire tip 214 may be especially rounded or smoothed. Additionally or alternatively, the second portion 218 of the wire tip 214 may be constructed of a different material than the rest of the wire tip 214, such as conformable material that is less stiff than other portions of the wire tip 214, or less stiff than other, traditional in vivo materials. As such, the second portion 218 of the wire tip 214 may be considered "atraumatic."

In one embodiment, the first end 206 tubular structure 202 is tapered. Such an embodiment may be advantageous in that a taper on the first end 206 of the tubular structure 202 may help negotiate bends and avoid snagging on side branches. In another embodiment, the first end 206 of the tubular structure 202 includes a variable diameter. Such a configuration may help accommodate the revascularization device 138 without increasing the size of the catheter 200 and decreasing maneuverability and flexibility which may occur with a larger sized catheter. In one example, the variable diameter of the first end 206 of the tubular structure 202 may be accomplished by including an expandable elastomer in that section of the catheter 200. In another example, the variable diameter of the first end 206 of the tubular structure 202 may be accomplished by including a c-shape for that portion of the catheter 200. In yet another example, the variable diameter of the first end 206 of the tubular structure 202 may be accomplished by both including an expandable elastomer having a c-shape in that portion of the catheter 200. Other examples are possible as well.

Figure 4A:
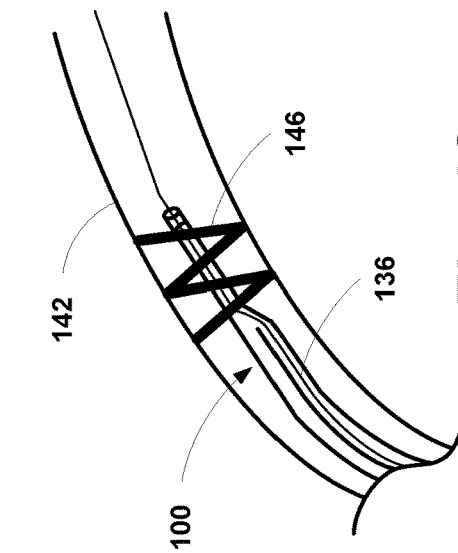
FIGS. 4A-4F illustrate the method steps of using the dual-lumen catheter of FIG. 1, according to an example embodiment.
Figure 4B:
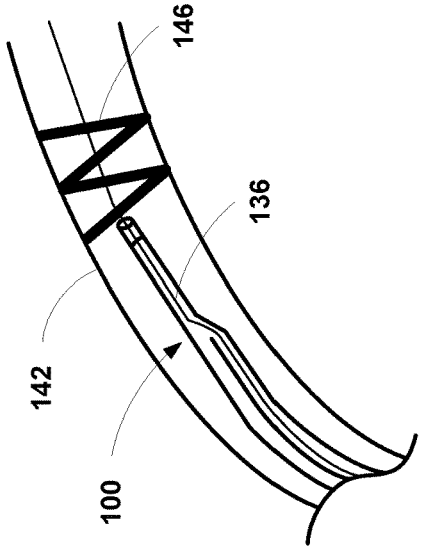
Figure 4C:
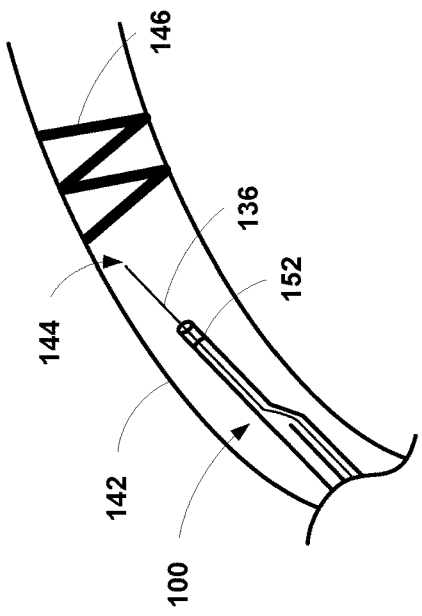
Figure 4D:
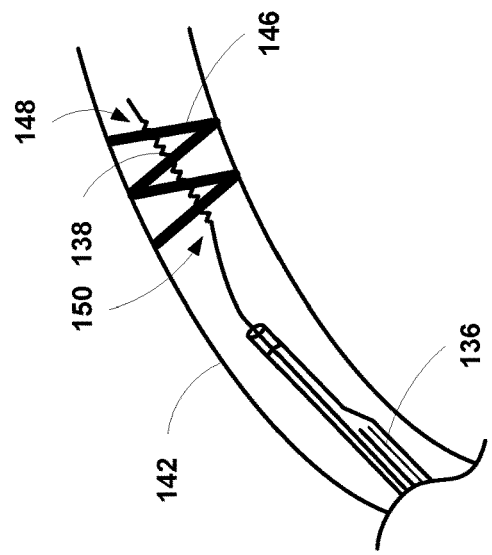
Figure 4E:
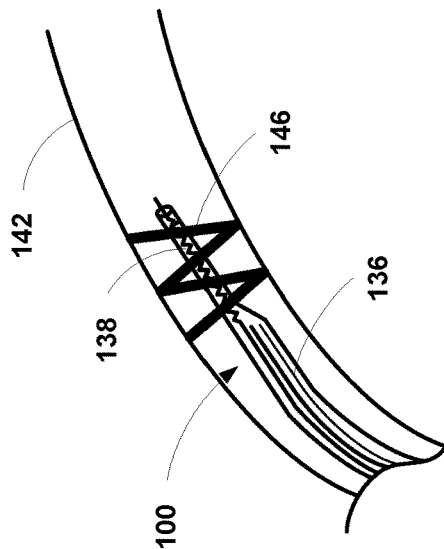
Figure 4F:
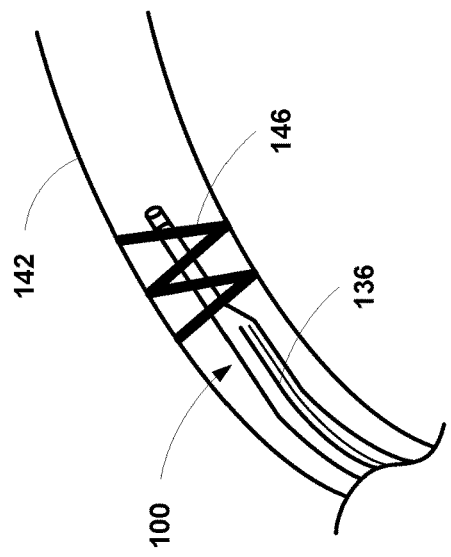

In operation, an example method includes introducing the catheter 100 according to the embodiments of FIG. 1 described above and a guidewire 136 together into an arterial configuration 142, such that a distal end 144 of the guidewire 136 extends distal to the first end 106 of the first tubular structure 102, as shown in FIG. 4A. Then, the catheter 100 and the guidewire 136 are advanced together through the arterial configuration 142 until the distal end 144 of the guidewire 136 is advanced across an occlusion 146 in the arterial configuration 142, as shown in FIG. 4B. Next, the catheter 100 is advanced with respect to the guidewire 136 in the arterial configuration 142 such that the first end 106 of the first tubular structure 102 is advanced across the occlusion 146, as shown in FIG. 4C. The distal end 144 of the guidewire 136 is then retracted into the first tubular structure 102 through the aperture 118 and into the second tubular structure 110, as shown in FIG. 4D. A revascularization device 138 is then advanced through the second end 108 of the first tubular structure 102 to the first end 106 of the first tubular structure 102, as shown in FIG. 4E. Finally, the catheter 100 is retracted relative to the neovascularization device 138 such that the revascularization device 138 is deployed into the arterial configuration 142 with a first end 148 of the revascularization device 138 located distal to the occlusion 146 and a second end 150 of the revascularization device 138 located proximal to the occlusion 146, as shown in FIG. 4F.

In one embodiment, the method may further include removing the revascularization device 138 from the arterial configuration 142 after a predetermined period of time, and determining whether the occlusion 146 has been removed from the arterial configuration 142. Such a determination may be made via fluoroscopy and digital subtraction angiography. The predetermined period of time is determined by current evidence data specific to the revascularization device 138. The method may further include, in response to a determination that the occlusion 146 has been removed from the arterial configuration 142, removing the guidewire 136 from the arterial configuration 142, and removing the catheter 100 from the arterial configuration 142.

In another embodiment, the method may further include, in response to a determination that the occlusion 146 has not been removed from the arterial configuration 142, re-advancing the distal end 144 of the guidewire 136 through the aperture 118 and into the first lumen 104 of the first tubular structure 102 and exiting the catheter 100 at the first end 106 of the first tubular structure 102. The method goes on to re-advance the first end 106 of the first tubular structure 102 across the occlusion 146 over the guidewire 136 such that the first end 106 of the first tubular structure 102 is located distal to the occlusion 146. Then, a second revascularization device 138 is advanced through the catheter 100, such that the second revascularization device 138 enters the catheter 100 at the second end 108 of the first tubular structure 102 and exits the catheter 100 at the first end 106 of the first tubular structure 102. Next, the second revascularization device 138 is introduced into the arterial configuration 142 such that a first end 148 of the second revascularization device 138 is located distal to the occlusion 146 and a second end 150 of the second revascularization device 138 is located proximal to the occlusion 146. Finally, the second revascularization device 138 is removed from the arterial configuration 142 after a predetermined period of time. This process may be repeated until it is determined that the occlusion 146 has been removed from the arterial configuration 142.

In another embodiment, the method may further include, in response to a determination that the occlusion 146 has not been removed from the arterial configuration 142, re-advancing the distal end 144 of the guidewire 136 through the aperture 118 and into the first lumen 104 of the first tubular structure 102 and exiting the catheter 100 at the first end 106 of the first tubular structure 102. The method goes on to re-advance the first end 106 of the first tubular structure 102 across the occlusion 146 over the guidewire 136 such that the first end 106 of the first tubular structure 102 is located distal to the occlusion 146. The method then goes on to re-advance the revascularization device 138 through the catheter 100, such that the revascularization device 138 enters the catheter 100 at the second end 108 of the first tubular structure 102 and exits the catheter 100 at the first end 106 of the first tubular structure 102. Then, the revascularization device 138 is introduced into the arterial configuration 142 such that a first end 148 of the revascularization device 138 is located distal to the occlusion 146 and a second end 150 of the revascularization device 138 is located proximal to the occlusion 146. Finally, the revascularization device 138 is removed from the arterial configuration 142 after a predetermined period of time. This process may be repeated until it is determined that the occlusion 146 has been removed from the arterial configuration 142.

In another embodiment, the method further includes, after retracting the distal end 144 of the guidewire 136 into the first tubular structure 102 through the aperture 118 and into the second tubular structure 110, retracting the guidewire 136 along with the catheter 100. In one embodiment of any of the methods described above, the distal end 144 of the guidewire 136 is retracted into the second tubular structure 110 at least a distance corresponding to a length of the occlusion 146. Further, retracting the distal end 144 of the guidewire 136 into the first tubular structure 102 through the aperture 118 and into the second tubular structure 110 further may comprise retracting the distal end 144 of the guidewire 136 out of the second end 116 of the second tubular structure 110 and into the arterial configuration 142. In such an embodiment, the method may further include re-advancing the distal end 144 of the guidewire 136 into the second end 116 of the second tubular structure 110.

In one embodiment that includes a locking device 152, the method may further comprise placing the locking device 152 in the locked mode prior to introducing the catheter 100 and the guidewire 136 together into the arterial configuration 142, and placing the locking device 152 in the unlocked mode prior to advancing the catheter 100 with respect to the guidewire 136 in the arterial configuration 142 such that the first end 106 of the first tubular structure 102 is advanced across the occlusion 146.

In another embodiment, an example method includes introducing a guidewire 136 into an arterial configuration 142 and through an occlusion 146 via arterial access, as shown in FIG. 5A. Then, the catheter 100 according to the embodiments of FIG. 2A described above is loaded onto the guidewire 136, onto the guidewire, such that a proximal end of the guidewire 136 enters the catheter 100 at the first end 106 of the first tubular structure 102, advances past the aperture 118 and into the second portion 122 of the first tubular structure 102 and exits at the second end 108 of the first tubular structure 102, as shown in FIG. 5B. Next, the catheter 100 is advanced along the guidewire 136 and catheter 100 is advanced into the arterial configuration 142 such that the first end 106 of the first tubular structure 102 is advanced across the occlusion 146, as shown in FIG. 5C. A revascularization device 138 is then advanced through the second end 108 of the first tubular structure 102, through the aperture 118, and into first end 106 of the first tubular structure 102, as shown in FIG. 5D. Finally, the catheter 100 is retracted relative to the neovascularization device 138 such that the revascularization device 138 is deployed into the arterial configuration 142 with a first end 148 of the revascularization device 138 located distal to the occlusion 146 and a second end 150 of the revascularization device 138 located proximal to the occlusion 146, as shown in FIG. 5E.

In another embodiment, an example method includes introducing a guidewire 136 into an arterial configuration 142 and through an occlusion 146 via arterial access, as shown in FIG. 6A. Then, the catheter 100 according to the embodiments of FIG. 2B described above is loaded onto the guidewire 136, such that a proximal end of the guidewire 136 enters the catheter 100 at the first end 106 of the first tubular structure 102, advances through the aperture 118 and into the second lumen 112 of the second tubular structure 110 and exits at the second end 116 of the second tubular structure 110, as shown in FIG. 6B. The baffle 139 may help guide the guidewire 136 through the aperture 118, as discussed above. Next, the catheter 100 is advanced along the guidewire 136 and catheter 100 is advanced into the arterial configuration 142 such that the first end 106 of the first tubular structure 102 is advanced across the occlusion 146, as shown in FIG. 6C. A revascularization device 138 is then advanced through the second end 108 of the first tubular structure 102 to the first end 106 of the first tubular structure 102, as shown in FIG. 6D. Finally, the catheter 100 is retracted relative to the neovascularization device 138 such that the revascularization device 138 is deployed into the arterial configuration 142 with a first end 148 of the revascularization device 138 located distal to the occlusion 146 and a second end 150 of the revascularization device 138 located proximal to the occlusion 146, as shown in FIG. 6E.

As such, some of the methods place the guidewire 136 in the arterial configuration 142 first, and then the catheter 100 is advanced over the guidewire 136 to the occlusion 146 in the arterial configuration 142. Such a method can be shown in FIGS. 5A-5E and FIGS. 6A-6E. Alternative methods describe a scenario where the guidewire 100 and catheter 100 are advanced together to the arterial configuration 142. In such an embodiment, the catheter 100 is locked so that the catheter 100 does not move with respect to the guidewire 136 as the catheter/guidewire combination is advanced to the arterial configuration 142. Such a method can be shown in FIGS. 4A-4F.

Figure 7A:
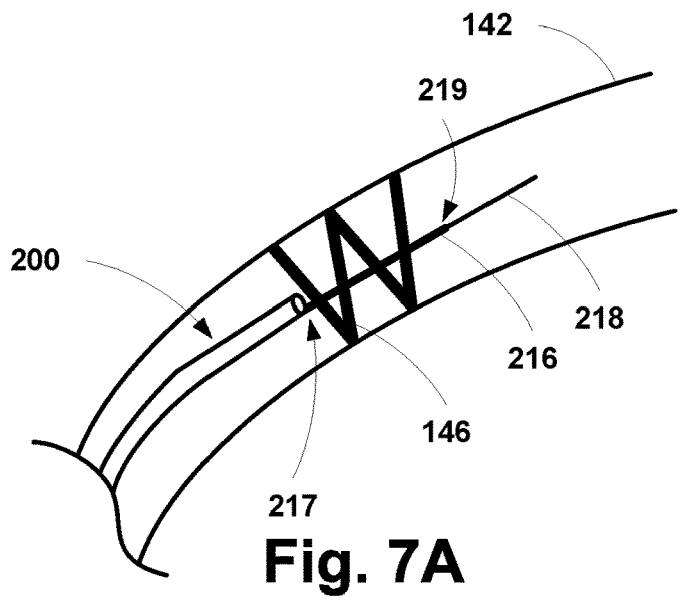
FIGS. 7A-7C illustrate the method steps of using the catheter of FIG. 3, according to an example embodiment.
Figure 7B:
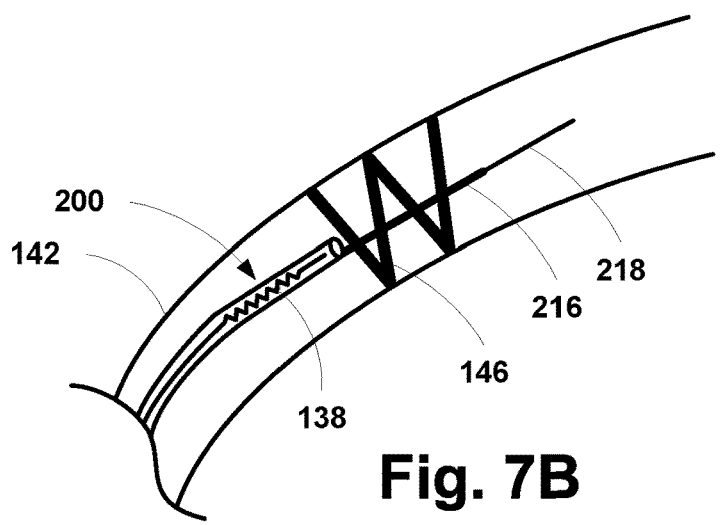
Figure 7C:
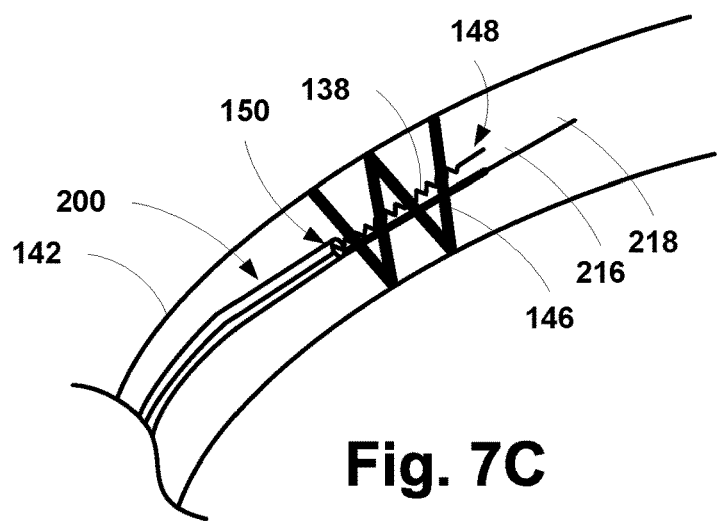

In yet another embodiment, an example method includes introducing the catheter 200 according to the embodiments of FIG. 3 described above into an arterial configuration 142 such that the wire tip 214 and the first end 206 of the tubular structure 202 is advanced across an occlusion 146, where a first end 217 of the first portion 218 of the wire tip 214 is located distal to the occlusion 146 and a second end 219 of the first portion 218 of the wire tip 214 is located proximal to the occlusion 146 when the wire tip 214 is advanced across the occlusion 146, as shown in FIG. 7A. A revascularization device 138 is then advanced through the second end 208 of the tubular structure 202 to the first end 206 of the first tubular structure 202, as shown in FIG. 7B. Finally, the revascularization device 138 is then advanced across the occlusion 146 such that the revascularization device 138 is deployed into the arterial configuration 142 with a first end 148 of the revascularization device 138 located distal to the occlusion 146 and a second end 150 of the revascularization device 138 located proximal to the occlusion 146, as shown in FIG. 7C. As the revascularization device 138 is deployed into the arterial configuration 142, the revascularization device 138 jails the first portion 218 of the wire tip 214. The occlusion 146, revascularization device 138, and catheter 200 may then be removed from the arterial configuration 142 substantially simultaneously.

It will be appreciated that other arrangements are possible as well, including some arrangements that involve more or fewer steps than those described above, or steps in a different order than those described above.

While various aspects and embodiments have been disclosed herein, other aspects and embodiments will be apparent to those skilled in the art. All embodiments within and between different aspects of the invention can be combined unless the context clearly dictates otherwise. The various aspects and embodiments disclosed herein are for purposes of illustration and are not intended to be limiting, with the true scope and spirit being indicated by the claims.

The invention claimed is:

1. A catheter comprising:
   a first tubular structure defining a first lumen, the first tubular structure having a first end and a second end;
   a second tubular structure defining a second lumen, the second tubular structure having a first end and a second end;
   an aperture between the first tubular structure and the second tubular structure, the aperture located at the first end of the second tubular structure, wherein a first portion of the first tubular structure extends between the aperture and the first end of the first tubular structure, wherein a second portion of the first tubular structure is coupled to and along a length of the second tubular structure such that the first tubular structure and the second tubular structure share an internal wall having a first end at the aperture and a second end at the second end of the second tubular structure, and wherein a stiffness of an entirety of the first portion of the first tubular structure is less than a stiffness of the second portion of the first tubular structure and a stiffness of the second tubular structure; and a baffle coupled to the first end of the internal wall, wherein the baffle obstructs the first lumen of the first tubular structure in a first position, and wherein the baffle is rotatably coupled to the internal wall from the first position to a second position in which the baffle does not obstruct the first lumen of the first tubular structure; and a locking device positioned at the first end of the first tubular structure, wherein the locking device is configured to prevent the catheter from moving with respect to a guidewire positioned in the first tubular structure in a locked mode, wherein the locking device is configured to allow the catheter to move along the guidewire in an unlocked mode, wherein the locking device is configured to be positioned in the locked mode prior to introducing the catheter and the guidewire together into an arterial configuration, and wherein the locking device is configured to be positioned in the unlocked mode prior to advancing the catheter with respect to the guidewire in the arterial configuration.

2. The catheter of claim 1, wherein the second portion of the first tubular structure and the second tubular structure each comprise a first material, and wherein the first portion of the first tubular structure comprises a second material that is different than the first material.

3. The catheter of claim 1, wherein a thickness of the first portion of the first tubular structure is less than a thickness of the second portion of the first tubular structure and a thickness of the second tubular structure.

4. The catheter of claim 1, wherein a longitudinal axis of the first lumen is parallel to a longitudinal axis of the second lumen at a given location along the length of the first tubular structure and the second tubular structure.

5. The catheter of claim 1, wherein the first end of the second tubular structure comprises a first opening, wherein the second end of the first tubular structure comprises a second opening, and wherein the second end of the second tubular structure comprises a third opening.

6. The catheter of claim 1, wherein the first end of the second tubular structure comprises an angled surface arranged to provide an angled transition from the second lumen to the first lumen through the aperture.

7. The catheter of claim 1, wherein the first end of the second tubular structure comprises a rounded surface arranged to provide a rounded transition from the second lumen to the first lumen through the aperture.

8. The catheter of claim 1, wherein the first portion the first tubular structure is tapered.

9. The catheter of claim 1, wherein the first portion of the first tubular structure includes a variable diameter.

10. The catheter of claim 1, wherein the catheter includes a plurality of metal strands arranged longitudinally or helically along at least a portion of a length of one or both of the first tubular structure and the second tubular structure.

11. The catheter of claim 10, wherein the plurality of metal strands comprises stainless steel, cobalt chromium, nitinol, or a combination thereof.

12. The catheter of claim 10, wherein the plurality of metal strands are braided.

13. The catheter of claim 10, wherein the plurality of metal strands comprise strips.

14. The catheter of claim 10, wherein a portion of the plurality of metal strands arranged along the second portion of the first tubular structure and the second tubular structure are wider than a portion of the plurality of metal strands arranged along the first portion of the first tubular structure.

15. The catheter of claim 10, wherein a portion of the plurality of metal strands arranged along the second portion of the first tubular structure and the second tubular structure are thicker than a portion of the plurality of metal strands arranged along the first portion of the first tubular structure.

16. The catheter of claim 1, wherein the first lumen has a length ranging from about 30 cm to about 170 cm.

17. The catheter of claim 1, wherein a diameter of the second portion of the first tubular structure has a range from about 0.35 mm to about 6 mm.

18. The catheter of claim 1, wherein the second tubular structure has a length ranging from about 5 cm to about 160 cm.

19. The catheter of claim 1, wherein a diameter of the second tubular structure has a range from about 0.25 mm to about 1.2 mm.

20. The catheter of claim 1, wherein the first portion of the first tubular structure has a length ranging from about 3 cm to about 25 cm.

21. The catheter of claim 1, wherein a diameter of the first portion of the first tubular structure has a range from about 0.35 mm to about 6 mm.

22. The catheter of claim 1, wherein the first portion of the first tubular structure has a radius of curvature ranging from about 0 mm to about 170 mm.

23. A method comprising:
introducing the catheter according to claim 1 and the guidewire together into the arterial configuration, wherein a distal end of the guidewire extends distal to the first end of the first tubular structure;
advancing the catheter and the guidewire together through the arterial configuration until the distal end of the guidewire is advanced across an occlusion in the arterial configuration;
advancing the catheter with respect to the guidewire in the arterial configuration such that the first end of the first tubular structure is advanced across the occlusion;
retracting the distal end of the guidewire into the first tubular structure through the aperture and into the second tubular structure;
advancing a revascularization device through the second end of the first tubular structure to the first end of the first tubular structure; and
retracting the catheter relative to the revascularization device such that the revascularization device is deployed into the arterial configuration with a first end of the revascularization device located distal to the occlusion and a second end of the revascularization device located proximal to the occlusion.

24. The method of claim 23, further comprising:
removing the revascularization device from the arterial configuration after a predetermined period of time; and
determining whether the occlusion has been removed from the arterial configuration.

25. The method of claim 24, further comprising:
in response to a determination that the occlusion has been removed from the arterial configuration, removing the guidewire from the arterial configuration; and
removing the catheter from the arterial configuration.

26. The method of claim 24, further comprising:
in response to a determination that the occlusion has not been removed from the arterial configuration, re-advancing the distal end of the guidewire through the aperture and into the first lumen of the first tubular structure and exiting the catheter at the first end of the first tubular structure;

re-advancing the first end of the first tubular structure across the occlusion over the guidewire such that the first end of the first tubular structure is located distal to the occlusion;

advancing a second revascularization device through the catheter, such that the second revascularization device enters the catheter at the second end of the first tubular structure and exits the catheter at the first end of the first tubular structure;

introducing the second revascularization device into the arterial configuration such that a first end of the second revascularization device is located distal to the occlusion and a second end of the second revascularization device is located proximal to the occlusion; and removing the second revascularization device from the arterial configuration after a predetermined period of time.

27. The method of claim 24, further comprising:

in response to a determination that the occlusion has not been removed from the arterial configuration, re-advancing the distal end of the guidewire through the aperture and into the first lumen of the first tubular structure and exiting the catheter at the first end of the first tubular structure;

re-advancing the first end of the first tubular structure across the occlusion over the guidewire such that the first end of the first tubular structure is located distal to the occlusion;

re-advancing the revascularization device through the catheter, such that the revascularization device enters the catheter at the second end of the first tubular structure and exits the catheter at the first end of the first tubular structure;

introducing the revascularization device into the arterial configuration such that a first end of the revascularization device is located distal to the occlusion and a second end of the revascularization device is located proximal to the occlusion; and removing the revascularization device from the arterial configuration after a predetermined period of time.

28. The method of claim 23, further comprising, after retracting the distal end of the guidewire into the first tubular structure through the aperture and into the second tubular structure, retracting the guidewire along with the catheter.

29. The method of claim 23, wherein the distal end of the guidewire is retracted into the second tubular structure at least a distance corresponding to a length of the occlusion.

30. The method of claim 23, wherein retracting the distal end of the guidewire into the first tubular structure through the aperture and into the second tubular structure further comprises retracting the distal end of the guidewire out of the second end of the second tubular structure and into the arterial configuration.

31. The method of claim 30, further comprising:

re-advancing the distal end of the guidewire into the second end of the second tubular structure.

32. A method comprising:

introducing a guidewire into an arterial configuration and through an occlusion via arterial access;

loading the catheter according to claim 1 onto the guidewire, such that a proximal end of the guidewire enters the catheter at the first end of the first tubular structure, advances past the aperture and into the second portion of the first tubular structure and exits at the second end of the first tubular structure;

advancing the catheter along the guidewire and introducing the catheter into the arterial configuration such that the first end of the first tubular structure is advanced across the occlusion;

advancing a revascularization device through the second end of the second tubular structure, through the aperture, and into the first end of the first tubular structure; and retracting the catheter relative to the revascularization device such that the revascularization device is deployed into the arterial configuration with a first end of the revascularization device located distal to the occlusion and a second end of the revascularization device located proximal to the occlusion.

33. A method comprising:

introducing a guidewire into an arterial configuration and through an occlusion via arterial access;

loading the catheter according to claim 1 onto the guidewire, such that a proximal end of the guidewire enters the catheter at the first end of the first tubular structure, advances through the aperture and into the second lumen of the second tubular structure and exits at the second end of the second tubular structure;

moving the catheter along the guidewire and introducing the catheter into the arterial configuration such that the first end of the first tubular structure is advanced across the occlusion;

advancing a revascularization device through the second end of the first tubular structure to the first end of the first tubular structure; and retracting the catheter relative to the revascularization device such that the revascularization device is deployed into the arterial configuration with a first end of the revascularization device located distal to the occlusion and a second end of the revascularization device located proximal to the occlusion.

* * * * *